(12) United States Patent
Tuschel et al.

(10) Patent No.: US 7,411,672 B2
(45) Date of Patent: Aug. 12, 2008

(54) METHOD AND APPARATUS FOR CHEMICAL IMAGING IN A MICROFLUIDIC CIRCUIT

(75) Inventors: David Tuschel, Monroeville, PA (US); Thomas Voigt, Export, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

(21) Appl. No.: 11/824,878

(22) Filed: Jul. 3, 2007

(65) Prior Publication Data

US 2007/0258089 A1 Nov. 8, 2007

Related U.S. Application Data

(63) Continuation of application No. 10/920,320, filed on Aug. 18, 2004, and a continuation of application No. 11/399,032, filed on Apr. 6, 2006, which is a continuation of application No. 10/882,082, filed on Jun. 30, 2004, now Pat. No. 7,046,359.

(51) Int. Cl.
  *G01J 3/44* (2006.01)
  *G01N 21/64* (2006.01)
  *G01N 21/65* (2006.01)
(52) U.S. Cl. .............. 356/301; 356/417; 250/458.1; 250/339.07; 435/288.7; 436/172
(58) Field of Classification Search ........... 356/301, 356/317, 318, 417
  See application file for complete search history.

(56) References Cited

U.S. PATENT DOCUMENTS

| | | | |
|---|---|---|---|
| 4,660,151 A | 4/1987 | Chipman et al. |
| 4,701,838 A | 10/1987 | Swinkels et al. |
| 4,766,551 A | 8/1988 | Begley |
| 4,885,697 A | 12/1989 | Hubner |
| 5,072,338 A | 12/1991 | Hug et al. |
| 5,121,337 A | 6/1992 | Brown |
| 5,121,338 A | 6/1992 | Lodder |
| 5,124,932 A | 6/1992 | Lodder |

(Continued)

FOREIGN PATENT DOCUMENTS

WO  CA98/00092  8/1998

(Continued)

OTHER PUBLICATIONS

Treado eta l., "Indium Antimonide (InSb) Focal Plane Array (FPA) Detection for Near-Infrared Imaging Microscopy," Applied Spectroscopy 48 (1994) p. 607.

(Continued)

*Primary Examiner*—F. L. Evans
(74) *Attorney, Agent, or Firm*—Morgan Lewis & Bockius LLP (57) ABSTRACT

The disclosure generally relates to a system for detecting a change in an attribute of a substance. The system may include a photon source for producing a first of a plurality of photons which interact with the substance while an attribute of the substance changes to produce a second plurality of photons. The system may also include a filter for receiving the collected photons and providing filtered photons; a photon detector for receiving the filtered photons and obtaining therefrom a spectrum of the substance; and a processor for detecting an aspect of the filtered photons wherein the aspect of the filtered photons is the function of the attribute of the substance.

32 Claims, 4 Drawing Sheets

U.S. PATENT DOCUMENTS

| | | | |
|---|---|---|---|
| 5,311,445 A | 5/1994 | White | |
| 5,324,567 A | 6/1994 | Bratchley et al. | |
| 5,377,003 A | 12/1994 | Lewis et al. | |
| 5,481,476 A | 1/1996 | Windig | |
| 5,528,393 A | 6/1996 | Sharp et al. | |
| 5,606,164 A | 2/1997 | Price et al. | |
| 5,610,836 A | 3/1997 | Alsmeyer et al. | |
| 5,626,134 A | 5/1997 | Zuckerman | |
| 5,710,713 A | 1/1998 | Wright et al. | |
| 5,751,415 A | 5/1998 | Smith et al. | |
| 5,784,162 A | 7/1998 | Cabib et al. | |
| 5,822,219 A | 10/1998 | Chen et al. | |
| 5,866,430 A | 2/1999 | Grow | |
| 5,910,816 A | 6/1999 | Fontenot et al. | |
| 6,002,476 A | 12/1999 | Treado | |
| 6,008,888 A | 12/1999 | Nottke et al. | |
| 6,052,187 A | 4/2000 | Krishnan et al. | |
| 6,069,690 A | 5/2000 | Xu et al. | |
| 6,175,750 B1 | 1/2001 | Cook et al. | |
| 6,181,414 B1 | 1/2001 | Raz et al. | |
| 6,239,904 B1 | 5/2001 | Serfling et al. | |
| 6,274,871 B1 | 8/2001 | Dukor et al. | |
| 6,300,618 B1 | 10/2001 | Tanaami et al. | |
| 6,358,387 B1 * | 3/2002 | Kopf-Sill et al. | 204/603 |
| 6,483,641 B1 | 11/2002 | MacAulay | |
| 6,485,413 B1 | 11/2002 | Boppart et al. | |
| 6,485,981 B1 | 11/2002 | Fernandez | |
| 6,549,861 B1 | 4/2003 | Mark et al. | |
| 6,584,413 B1 | 6/2003 | Keenan et al. | |
| 6,640,130 B1 | 10/2003 | Freeman et al. | |
| 6,640,132 B1 | 10/2003 | Freeman et al. | |
| 6,697,665 B1 | 2/2004 | Rava et al. | |
| 6,741,884 B1 | 5/2004 | Freeman et al. | |
| 6,810,279 B2 | 10/2004 | Mansfield et al. | |
| 6,937,885 B1 | 8/2005 | Lewis et al. | |
| 6,939,686 B2 | 9/2005 | Ling et al. | |
| 7,046,359 B2 | 5/2006 | Voigt et al. | |

OTHER PUBLICATIONS

Morris, Hoyt, Miller and Treado, "Liquid Crystal Tunable Filter Raman Chemical Imaging," Applied Spectroscopy, vol. 50, No. 6, (Jun. 1996) pp. 805-811.
Patrick J. Treado, "Chemical Imaging Reveals More than the Microscope," Laser Focus World, (Oct. 1995) pp. 1-7.
Morris, "Ultrasensitive Raman and Fluorence Imaging Using LIquid Crystal Tunable Filters," SPIE vol. 2385, (1995) pp. 81-87.
Treado et al., "Infrared Raman Spectroscopic Imaging," (Marcell Decker, 1992) pp. 71-108.
Treado et al., "High-Fidelity Raman Imaging Spectrometry: A Raid Method Using an Acousto-Optic Tunable Filter," Applied Spectroscopy, vol. 46, No. 8 (1992) pp. 1211-1216.
Treado et al., "Near Infrared Acousto-Optic Filtered Spectroscopic Microscop: A Solid-State Approach to Chemical Imaging," Applied Spectroscopy, vol. 46, No. 4 (1992) pp. 553-559.
Morris et al., "Imaging Spectrometers for Fluorescence and Raman Microscopy: Acousto-Optic and Liquid Crystal Tunable Filters," Applied Spectroscopy, vol. 48, No. 7 (1994) pp. 857-860.
Turner et al., "LCTF Raman Chemical Imaging in the Near-Infrared," SPIE vol. 3061 (1997) pp. 280-283.
Miller et al., "Multispectral Imaging with a Liquid Crystal Tunable Filter," SPIE vol. 2345, (1995) pp. 354-365.
Ling et al., "Direct Raman Imaging Techniques for Study of the Subcellular Distribution of a Drug," Applied Optics, vol. 41, No. 28, (2002) pp. 6006-6017.
Conti, S., et al., "Traces of polymethylsiloxane in case histories of rape: technique for detection," Elsvier Science Ireland Ltd., Forensic Science International, Jan. 1995, pp. 121-128.
Lee, G.S.H., et al., "A Methodology Based on NMR Spectroscopy for the Forensic Analysis of Condoms," St. Andrews Centre for Advanced Materials, pp. 808-821. no date.
Maynard, P., et al., "A protocol for the forensic analysis of condom and personal lubricants found in sexual assault cases," Forensic Science International, 124 (2001), pp. 140-156.
Stoilovic, M., et al., "The Application of Light in Forensic Science & A Modern Approach to Fingerprint Detection and Enhancement," Australian Federal Police, AFP Workshop Manual, Oct. 2000.
Roux, C., et al., "Evaluation of 1,2-Indanedione and 5,6-Dimethoxy-1,2-Indanedione for the Detection of Latent Fingerprints on Porous Surfaces," Journal of Forensic Sciences, vol. 45(4), 2000, pp. 761-769.
Roux, C., et al., "A study to investigate the evidential value of blue and black ballpoint pen inks in Australia," Forensic Science International, 101 (1999), pp. 167-176.
Mazzella, W.D., et al., "Classification and Identification of Photocopying Toners by Diffuse Reflectance Infrared Fourier Transform Spectroscopy (DRIFTS): I. Preliminary Results," Journal of Forensic Sciences, JFSCA, vol. 36, No. 2, Mar. 1991, pp. 449-465.
Mazzella, W.D., et al., "Classification and Identification of Photocopying Toners by Diffuse Reflectance Infrared Fourier Transform Spectroscopy (DRIFTS): II. Final Report," Journal of Forensic Sciences, JFSCA, vol. 36, No. 3, May 1991, pp. 820-837.
Brunelle, R.L., "Questioned Document Examination," Bureau of Alcohol, Tobacco and Firearms, U.S. Treasury Department, 1982.
Robertson, J., et al., "The Persistence of Textile Fibres Transferred During Simulated Contacts," Journal of Forensic Sciences, vol. 22, No. 4, Oct. 1982, pp. 353-360.
Gaudette, B.D., "The Forensic Aspects of Textile Fiber Examination," Central Forensic Laboratory, Royal Canadian Mounted Police. no date.
Pounds, C.A., et al., "The Transfer of Fibres between Clothing Materials During Simulated Contacts and their Persistence During Wear: part I - Fibre Transference," Journal of Forensic Sciences, vol. 15, 1975, pp. 17-27.
Pounds, C.A., et al., "The Transfer of Fibres between Clothing Materials During Simulated Contacts and their Persistence During Wear: Part II - Fibre Persistence," Journal of Forensic Sciences, vol. 15, pp. 29-37. 1975.
Maynard, P., et al., "Adhesive Tape Analysis: Establishing the Evidential Value of Specific Techniques," Journal of Forensic Sciences, vol. 46(2), 2001, pp. 280-287.
Caetano, M.R., et al., "Evaluation of the importance of non-linear spectral mixing in coniferous forests," EUROPTO Conference on Remote Sensing for Agriculture, Ecosystems, and Hydrology, Barcelona, Spain, Sep. 1998.
Rasmussen, G.T., et al., "Library Retrieval of Infrared Spectra Based on Detailed Intensity Information," Applied Spectroscopy, vol. 33, No. 4, 1979.
Guilment, J., et al., "Infrared Chemical Micro-Imaging Assisted by Interactive Self-Modeling Multivariate Analysis," Applied Spectroscopy, vol. 48. No. 3, 1994.
Engman, E.T., "Remote Sensing for Agriculture, Ecosystems, and Hydrology," Proceedings of SPIE EUROPTO Series, vol. 3499, Sep. 22-24, 1998.
Press, W.H., et al., Numerical Recipes in C; The Art of Scientific Computing, 2nd ed., Cambridge, NY: Cambridge University Press, 1992.
Malinowski, E.R., Factor Analysis in Chemistry, 2nd ed., New York, NY: John Wiley & Sons, Inc., 1991.
Zhang, C.X., et al., Biochips, Technology and Applications, "Trends in Microfluidic Devices for Analytical Chemistry," Springer-Verlag, 2004, pp. 101-134.
Shinohara, K., et al., "High-speed micro-PIV measurements of transient flow in microfluidic devices," Measurement of Science and Technology, vol. 15, 2004, pp. 1965-1970.

* cited by examiner

METHOD AND APPARATUS FOR CHEMICAL IMAGING IN A MICROFLUIDIC CIRCUIT

RELATED APPLICATIONS

The instant application is a continuation of U.S. patent application Ser. No. 10/920,320, filed Aug. 18, 2004 and entitled "Method and Apparatus for Chemical Imaging in a Microfluidic Circuit." The instant application is also a continuation of U.S. patent application Ser. No. 11/399,032, filed Apr. 6, 2006, and entitled "System and Method for Dynamic Chemical Imaging" which is a continuation of U.S. patent application Ser. No. 10/882,082, filed Jun. 30, 2004, now U.S. Pat. No. 7,046,359, and entitled "System and Method for Dynamic Chemical Imaging". Each of the above-identified applications is assigned to the assignee of the present application. Each of the above-referenced applications is incorporated herein in its entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

Conventional imaging system include a slide for receiving the sample, a light source for illuminating the sample with a plurality of photons, a lens for receiving the photons scattered (or emitted) by the sample, a tunable filter and an image sensor for forming a three dimensional image of the sample. During operation, the sample is placed on a microscopic slide or a Petri dish and placed at a designated location where photons emitted or scattered from the sample can be collected by an objective lens. The conventional imaging spectrometers are configured to obtain an image of a sample in a homeostasis. That is, the conventional imaging systems are directed to detecting an image from a samples in a state of physical and/or chemical equilibrium with a tendency to remain in such state. There is a need for a method and apparatus for chemical imaging of a dynamic system.

SUMMARY OF THE DISCLOSURE

In one embodiment, the disclosure relates to a system for detecting a change in an attribute of a substance. The system may include a photon source for a first of a plurality of photons which interact with the substance while an attribute of the substance changes to thereby produce a second plurality of photons; a filter for receiving the collected photons and providing therefrom filtered photons; a photon detector for receiving the filtered photons and obtaining therefrom a spectrum of the substance; and a processor for detecting an aspect of the filtered photons wherein the aspect of the filtered photons is the function of the attribute of the substance.

In another embodiment, the disclosure relates to a system for detecting a change in attribute of a substance in a dynamic system. The system can include a photon source for providing a first plurality of photons which interact with the substance and produce a second plurality of photons; a microfluidic circuit for collecting said second plurality of photons; a microfluidic circuit through at least a portion of which the substance passes while the attribute of the substance changes; an optical lens for collecting the second plurality of photons; a filter for receiving the collected photons and providing therefrom filtered photons; a photon detector for receiving the filtered photons and obtaining therefrom a spectrum of the substance; and a processor for determining an aspect of the filtered photons wherein the aspect of the filtered photons is a function of the attribute of the substance, to thereby determine a change in the attribute of the substance.

In a method according to an embodiment of the disclosure, a change in the attribute of a substance is determined by illuminating the substance with a first plurality of photons which interact with the substance while an attribute of the substance changes to thereby produce a second plurality of photons; collecting said second plurality of photons; receiving the collected photons and providing therefrom filtered photons; detecting the filtered photons and obtaining therefrom a spectrum of the substance and determining an aspect of the filtered photons wherein the aspect of the filtered photons is a function of the attribute of the substance to thereby determine a change in the attribute of the substance.

According to another embodiment, a method for detecting a change in an attribute of a substrate includes illuminating the substance with a first plurality of photons which interact with the substance while an attribute of the substance changes to thereby produce a second plurality of photons; collecting said plurality of photons; receiving the collected photons and providing therefrom filtered photons; detecting the filtered photons to obtain a spectrum of the substance and determining an aspect of the filtered photons. The aspect of the filtered photons can be a function of the attribute of the substance to thereby determine a change in the attribute of the substance.

DETAILED DESCRIPTION

Figure 1:
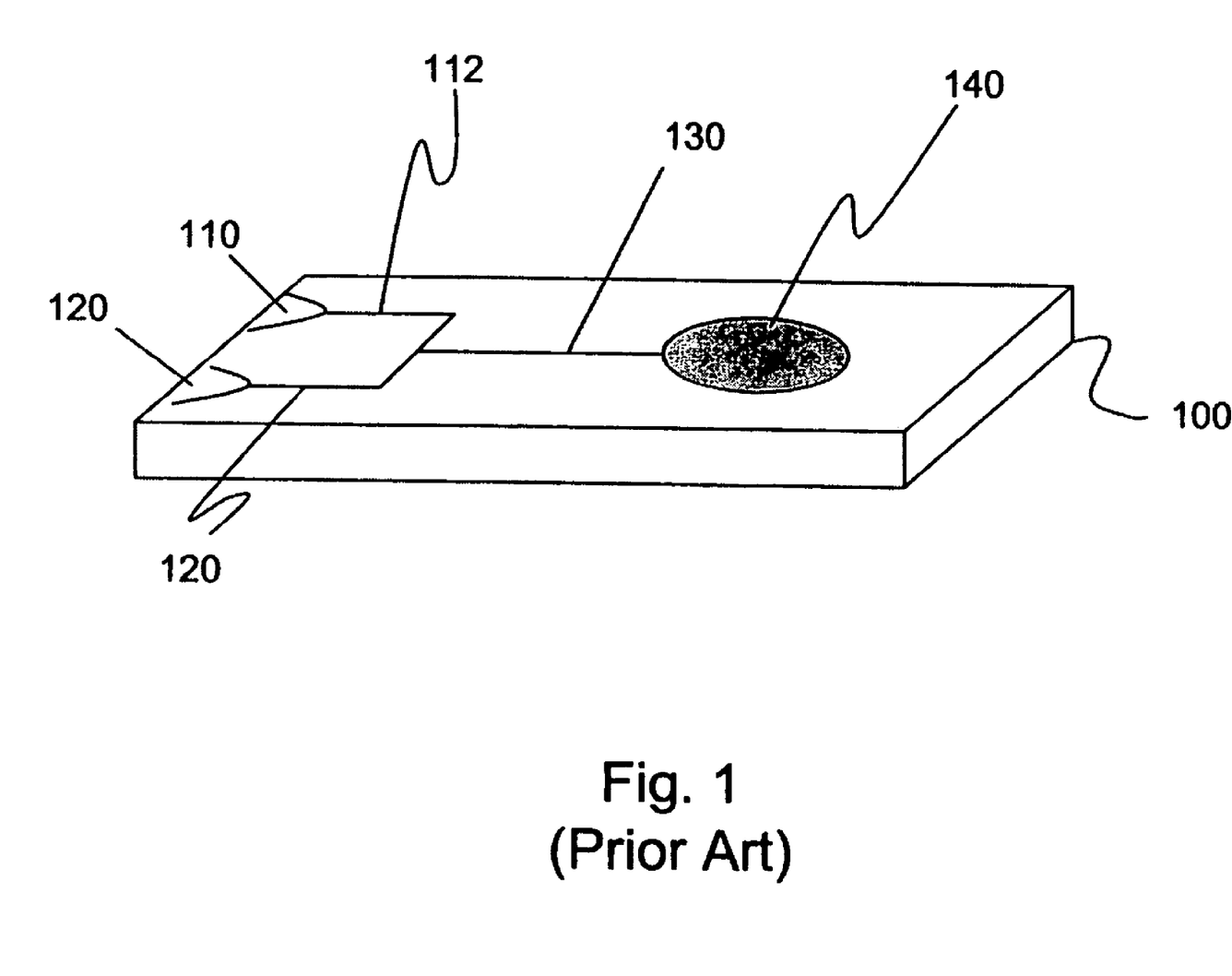
FIG. 1 is a schematic representation of a microfluidic circuit.

FIG. 1 is a schematic representation of a microfluidic circuit. The microfluidic circuit 100 is shown to have reservoirs or receptacles 110 and 120 communicating with channels 112 and 120, respectively. Channels 112 and 120 merge to form channel 130. Channel 130 is received by reservoir 140. Although not shown, reservoir 140 can include an exit channel for taking the mixture away from the reservoir. In addition, reservoir 140 may be replaced by extending channel 130 or by forming a serpentine channel to provide additional time for the reactants to admix. Each of reservoirs 110 and 120 can receive different reactants or reagents. When using a microfluidic circuit, the reaction dynamic may be a function of the microfluidic circuit as well as the rate of reaction. Thus, the circuit can be designed to receive a plurality of reagents, provide extended reaction time for some of the reagents or provide additional for controlling the rate of reaction. Microfluidic circuits have complex structures. As a result, the provide spatially-dependent chemical changes within the circuit that need to be monitored. In one embodiment, the disclosure enables monitoring and understanding such changes despite the complex spatial arrangement of the fluids within the microfluidic circuit.

Figure 2:
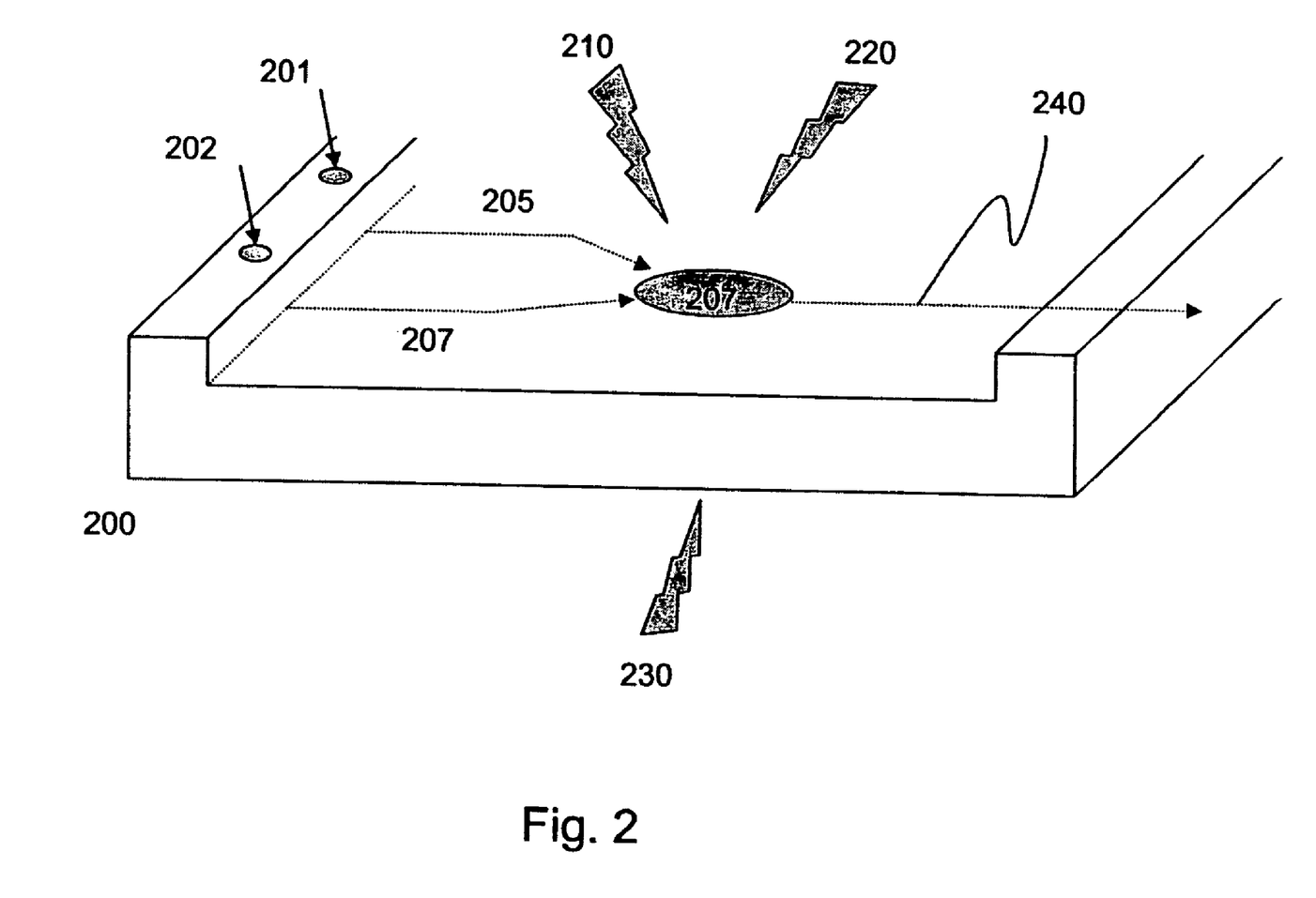
FIG. 2 shows another embodiment of a microfluidic circuit.

FIG. 2 shows another embodiment of a microfluidic circuit. In the embodiment shown in FIG. 2, receptacles 201 and 202 receive a first and a second reagent and, respectively, communicate the reagent through embedded channels 205 and 207 to region 207 of circuit 200. Region 207 can be a reservoir or a plurality of channels specifically designed to enhance mixing of the reagents. Illumination is shown as arrows 210, 220 and 230 directed to the mixing region 207. The mixture can be carried out though channel 240.

Figure 3:
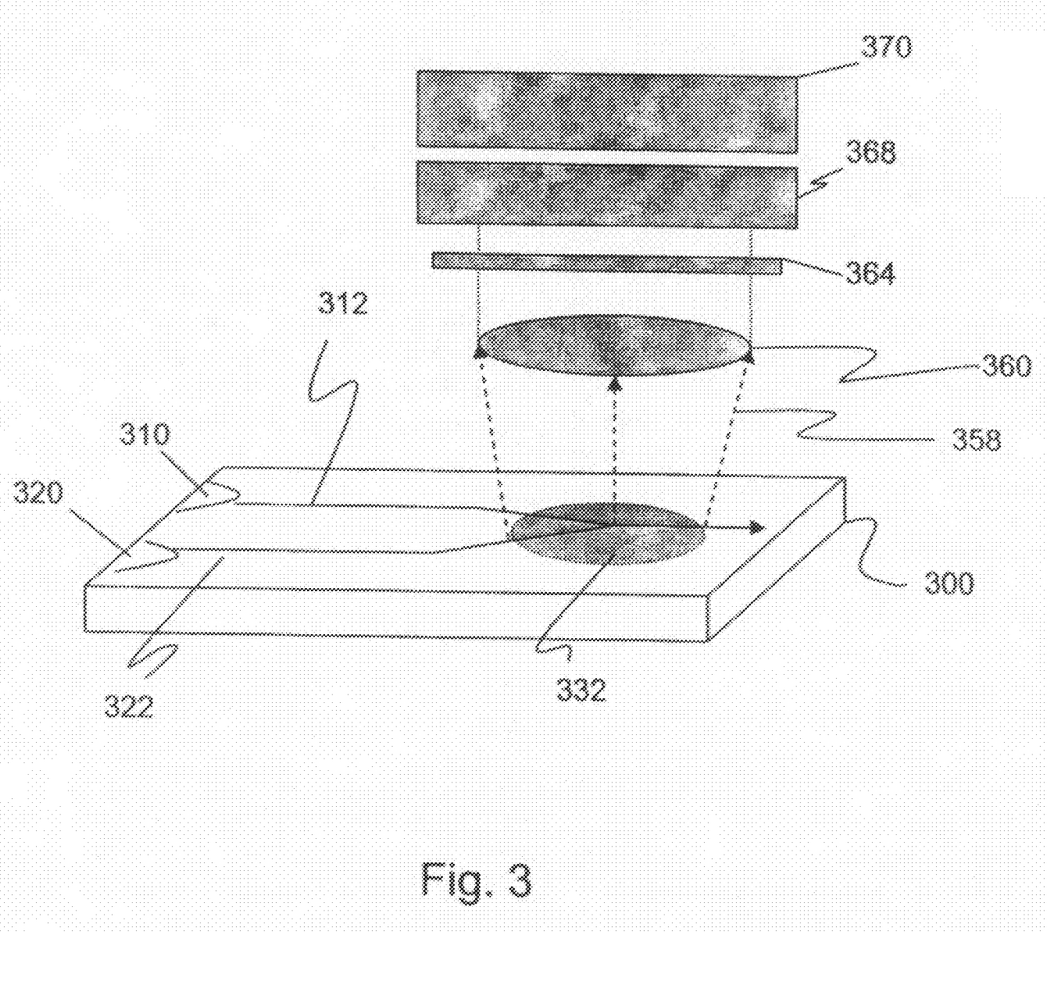
FIG. 3 shows a system according to one embodiment of the disclosure.

FIG. 3 shows a system according to one embodiment of the disclosure. Referring to FIG. 3, microfluidic circuit 300 includes reservoirs 310 and 320 each receiving a reactant (or a reagent). The reactants are directed to channels 312 and 322 prior to adjoining at region 332. In one embodiment, the substance under detection will enters and passes through at least a portion of detection region 332 while the attribute of the substance is changing. In other words, detection region 332 can be selected such that the substance is undergoing an attribute change while passing therethrough. Alternatively, detection region 332 can be selected further downstream or upstream to monitor and detect an attribute of the composition.

The substance can be one of a single molecule, a group of molecules, a chemical reagent or a fluid containing pathogens. In one embodiment, the substance is one of a single cell, an element, a compound, a molecule, a reactant, a solvent, a solute, a fluid or a biological substance. The attribute of the substance can relate to one or more of the following characteristics: a physical property, a chemical property, an electrical property, a magnetic property, an optical property or a biological property. For example, the attribute can define a physical structure, a physical orientation, a chemical structure, a chemical composition, a chemical state or an index of refraction. In one embodiment, the attribute is a combination of several identifiable characteristics.

Although not shown in the exemplary embodiment of FIG. 3, one or more radiation source (interchangeably, photon source) can be positioned about microfluidic circuit 300 to direct photons to detection region 332. The radiation used to illuminate the sample need not pass through optical lens 360 to illuminate the sample. For example, one or more light source can be positioned below circuit 300 so as to direct photons to detection region 332. Alternatively, one or more light source can be positioned above circuit 300 or at an oblique angle to circuit 300 so as to direct photons to detection region 332. This results is reduced internal scattering and attenuation of the incident exciting photons. The multitude of photons reaching detection region 332 can be absorbed by the sample, scatter upon reaching the sample or be emitted by the substance present at this region. The scattered or emitted photons are schematically shown by arrows 358.

In one embodiment, the photons source is selected from the group consisting of a laser and a light emitting diode. In another embodiment, the photon source can have a wavelength in one of the infrared, the near infrared, the visible, ultraviolet or x-ray wavelength range. In still another embodiment, the photon source is selected from the group consisting of electro-generated luminescence and chemi-luminescence. In still another embodiment, a plurality of photon sources is provided where each source provides photons in one or more of the above-cited exemplary wavelength ranges. In still another embodiment, a broadband photons sources is passed through a narrow-pass filter and then used as an illumination source. Thus, an exemplary spectrum can be one of a Raman, luminescence (e.g., fluorescence), near infrared, an infrared, ultraviolet or an x-ray spectrum. In one embodiment, the wavelength of the source is in the range of about 15-25 $cm^{-1}$.

Lens 360 is positioned above a region of the microfluidic circuit to receive optical emitted or scattered light by detection region 332. Lens 360 can be a single objective lens or it can be an objective train as used in microscopic or macroscopic devices. The color and the resolution of the viewed sample can be determined by the tunable filter and the resolution of the imaging detector. Thus, in one embodiment, the system can use a conventional high resolution, low aberration lens. Indeed, a simpler reduced resolution/aberration lens can be designed with larger numeral aperture to increase system throughput (light delivery and collection efficiency) while providing the same quality resolution as the conventional systems.

The photons received by lens 360 are then processed through one or more rejection filter 364. The rejection filter enables spectral filtering of light at the illuminating wavelength. Filter 364 can be selected from the group consisting of a notch filter, a bandpass filter or a spectral filter. Additionally, a laser rejection filter (not shown) can be positioned prior to rejection filter 364 to filter out scattered illumination light represented and to optimize the performance of the system.

Photons passing through rejection filter 364 are received by a wavelength imaging analyzer 368. The analyzer receives the plurality of photons from rejection filter 364 and produces an image therefrom. The image can be a 3-D image. A conventional tunable filter (including electro-optical tunable filters) including liquid crystal tunable filter ("LCTF") or acousto-optical tunable filter ("AOTF") can be used as analyzer 368. The electro-optical filters (interchangeably, tunable filters) allow specific wavelengths or ranges of wavelengths of light to pass through as an image, depending on the control signals placed on the device by a controller (not shown). The wavelengths that can be passed through tunable filter 368 may range from 200 nm (ultraviolet) to 2000 nm (i.e., the far infrared). The choice of wavelength depends on the desired optical region and/or the nature of the sample being analyzed.

Referring again to FIG. 3, photon detector 368 relays the images of the wavelength imaging analysis to wavelength detector 370. Wavelength detector 370 can be a charge-coupled device, a complementary metal oxide semiconductor, a charge injection device, an intensified charge injection device, an electron multiplying charge-coupled device, a photo diode, a silicon photo diode, a silicon avalanche diode or a camera. In one embodiment of the disclosure, the photon detector determines a change in the attributes of the substance by detecting an identifying an aspect of the received photons where an aspect of the received photons is a function of the attribute of the substance. By way of example, the aspect of the received photons can be, among others, a wavelength, frequency, phase, polarization, and intensity.

In another embodiment, detector 370 can be a two-dimensional, image focal plane array ("FPA"). The optical region employed to characterize the sample of interest governs the choice of FPA detector. For example, silicon charge-coupled device ("CCD") detectors can be employed with visible wavelength fluorescence and Raman spectroscopic imaging, while gallium arsenide (GaAs) and gallium indium arsenide (GaInAs) FPA detectors can be employed for image analyses at near infrared wavelengths. The choice of such devices depends on the type of sample being analyzed. Photon detector 370 produces digital images of the entire view of the sample as processed by analyzer 368. The digital images can be communicated to display devices or electronically transmitted to another network for further processing.

Figure 4:
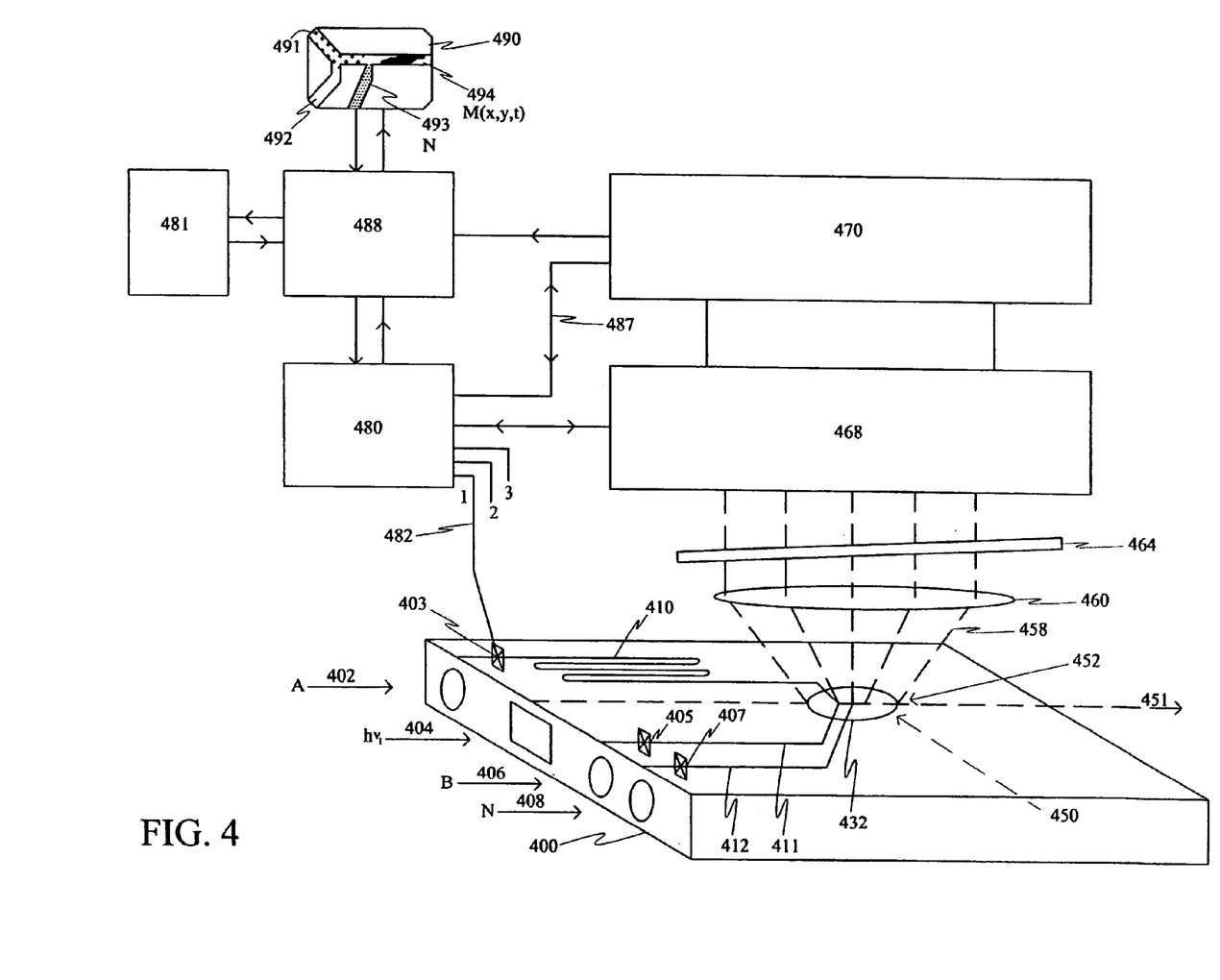
FIG. 4 is a detection system according to one embodiment of the disclosure.

FIG. 4 is a detection system according to one embodiment of the disclosure. More specifically, FIG. 4 shows an exemplary system for detecting pathogens in water. Referring to FIG. 4, microfluidic circuit 400 is shown to have input channels 402, 404, 406 and 408. The input channels 402, 406 and 408 may be used for introducing the various reagents into the system. Input channel 404 can be used to transmit laser, among others, through the system. In other words, input channel 404 can be coupled to a radiation source for illuminating to circuit 400. Valves 403, 405 and 407 are interposed in channels 402, 406 and 408, respectively, to regulate the flow of reagents into the system. In the embodiment of FIG. 4, the valves are controlled by controller 480 so as to meter the flow of each reagent.

Channels 410, 411 and 412 show the path traveled by each of the reagents prior to mixing. The layout of channels 410, 411 and 412 is exemplary in nature. Channel 410 is shown to have a serpentine path while channels 411 and 412 are shown with a relatively direct path to detection region 432. Detection region 432 is also the region where the reagents come in contact with each other to form a reaction mixture. In the exemplary embodiment of FIG. 4, reagent A admixes with reagent B and the resulting mixture which then reacts with reagent N. Thus, imaging region 432 represents a chemically dynamic region such that the imaging system of FIG. 4 can detect and report the attribute changes of the system as the reactants come in contact with each other.

To illuminate detection region 432, radiation sources 450 and 452 are respectively positioned below and above microfluidic circuit 400. The additional radiation source 404 is strategically positioned to illuminate the circuit from within by using a microfluidic channel that acts as a light pipe. A light pipe can arise from the different indexes of refraction between the fluid and the channel material in order to transport, and in some cases, focus the light to particular regions within the microfluidic circuit. The channels used as light pipes may have optical coating or carry special fluids to optimize the internal channeling of light to regions o interest. The regions of interest may lie inside the microfluidic circuit. The positioning of radiation source 404 can be particularly beneficial as it can provide radiation frequency different from those of sources 450 and 452. For example, radiation source 404 can be used to provide laser or fluorescence illumination while radiation sources 450 and 452 provide different radiation.

As in FIG. 3, the photons reaching the sample at the detection region can be scattered and/or emitted. The scattered and emitted photons are schematically shown as 458. The scattered and emitted photons are collected by lens 460 and are directed to rejection filter 464, analyzer 468 and detector 470.

In the exemplary embodiment of FIG. 4, analyzer 468 and detector 470 are shown to communicate with each other and with controller 480. The controller can be an integrated circuit programmed to execute instructions from a memory. The controller can be a stand-alone system (not shown) or can be coupled to a computer 488. Computer 488 can be a handheld device, a desktop computer or a network. In the exemplary embodiment of FIG. 4, computer 488 is coupled to databases 481 and display 490. In an alternative embodiment, computer 488 may be integrated with database 481 and display 490.

Database 480 can provide a data library to computer 488. Computer 488 can use data received from detector 470, controller 480 and database 481 not only to provide an output in the form display 490, but to also direct controller 480. In turn, controller 480 can optimize the operation of analyzer 168 and detector 470. In addition, controller 480 can provide flow control by metering fluid flow through each of valves 403, 405 and 407. For illustration, controller 480 is shown to be coupled to valve 403 through connection line 482. Although not shown, controller 480 can be independently coupled to each of valves 405 and 407.

Display 490, as shown in FIG. 4, is exemplary as it depicts detection region 432 with each of reagents A (491), reagent B (492) and reagent N (493). The region identified as 494 shows the reaction dynamics of the reagents A, B and N. In one embodiment, the image shown is a function of dimensions (x, y) and time. In other words, the images can depict a reaction as a function of time. The images can be saved for future viewing by computer 488. In an alternative embodiment, the images can be compared against the images in database 481 to identify or quantify the displayed reaction. In still another embodiment, computer 488 can record and display the images as a continuous stream of data.

The configurations disclosed herein are suitable for Raman imaging of micro fluid circuits or biological samples undergoing change. The disclosed configuration can also be used with multiple detection system simultaneously. For example, the detection system shown in FIG. 4 can be configured to receive and analyze Raman and fluorescent images simultaneously.

Although the principles disclosed herein have been described in relation with the non-exclusive exemplary embodiments provided herein, it should be noted that the principles of the disclosure are not limited thereto and include permutations and variations not specifically described.

What is claimed:

1. A system for determining a change in an attribute of a substance, the system comprising: a microfluidic circuit having a plurality of input channels integral thereto, wherein said substance is provided through a first one of said plurality of input channels; a photon source for providing a first plurality of photons through a second one of said plurality of input channels so as to internally illuminate a portion of said microfluidic circuit containing said substance, wherein said first plurality of photons interact with the substance while an attribute of the substance changes to thereby produce a second plurality of photons; an optical lens for collecting said second plurality of photons; a filter for receiving the collected photons and providing therefrom filtered photons having one or more predetermined wavelengths; and a processor for determining an aspect of the filtered photons wherein the aspect of the filtered photons is a function of the attribute of the substance, to thereby determine a change in the attribute of the substance.

2. The system of claim 1 wherein the attribute is selected from the group consisting of a physical property, a chemical property, an electrical property, a magnetic property, an optical property, and a biological property.

3. The system of claim 2 wherein the substance is a single molecule or a group of molecules.

4. The system of claim 1 wherein the attribute is at least one of the following: a physical structure; a physical orientation; a chemical structure; a chemical composition; a chemical state; and an index of refraction.

5. The system of claim 1 wherein the substance is selected from the group consisting of a cell, an element, a compound, a molecule, a reactant, a solvent, a solute, a fluid, and a biological substance.

6. The system of claim 1 wherein said photon source is selected from the group consisting of a laser and a light emitting diode.

7. The system of claim 6 wherein the first plurality of photons has a wavelength in one of the following wavelength ranges: the infrared wavelength range; the near infrared wavelength range; the ultraviolet wavelength range; the X-ray wavelength range; and the visible wavelength range.

8. The system of claim 1 wherein said filter is selected from the group consisting of a notch filter, a bandpass filter, a spectral filter, a tunable filter, a liquid crystal tunable filter, and an acousto-optical tunable filter.

9. The system of claim 1 wherein the interaction of the first plurality of photons with the substance is selected from the group consisting of scattering, emission, reflection, and refraction.

10. The system of claim 1 wherein said processor comprises software programmed to determine the aspect of the filtered photons.

11. The system of claim 1 wherein said processor comprises firmware programmed to determine the aspect of the filtered photons.

12. The system of claim 1, further comprising a photon detector for receiving the filtered photons and for providing therefrom a spectral image of the substance.

13. The system of claim 12, wherein the spectral image is one of the following: a Raman spectral image; a luminescence spectral image; a near infrared spectral image; an infrared spectral image; and an ultraviolet spectral image.

14. The system of claim 1, wherein said optical lens, said filter, and said processor are external to said microfluidic circuit.

15. The system of claim 1, wherein said aspect of the filtered photons is at least one of the following: a wavelength; a frequency; a phase; a polarization; and an intensity.

16. The system of claim 1, further comprising an illumination source placed external to said microfluidic circuit so as to externally illuminate said portion of said microfluidic circuit with a third plurality of photons, wherein said third plurality of photons interact with the substance while said attribute of the substance changes to thereby produce a fourth plurality of photons, wherein said optical lens is configured to collect said fourth plurality of photons, and wherein said filter is configured to receive said collected fourth plurality of photons and provide therefrom said filtered photons to said processor.

17. The system of claim 16, wherein said illumination source is different from said photon source.

18. The system of claim 16, wherein a wavelength of said third plurality of photons is different from a wavelength of said first plurality of photons.

19. The system of claim 16, wherein the third plurality of photons has a wavelength in one of the following wavelength ranges: the infrared wavelength range; the near infrared wavelength range; the ultraviolet wavelength range; the X-ray wavelength range; and the visible wavelength range.

20. The system of claim 12, wherein said photon detector is selected from the group consisting of a charge-coupled device, a complementary metal oxide semiconductor array, and a focal plane array.

21. A method for determining a change in an attribute of a substance provided through a first one of a plurality of input channels within a microfluidic circuit, the method comprising: illuminating the substance with a first plurality of photons provided through a second one of said plurality of input channels so as to internally illuminate a portion of said microfluidic circuit containing said substance, wherein said first plurality of photons interact with the substance while an attribute of the substance changes to thereby produce a second plurality of photons; collecting said second plurality of photons; receiving the collected photons and providing therefrom filtered photons having one or more predetermined wavelengths; and determining an aspect of the filtered photons wherein the aspect of the filtered photons is a function of the attribute of the substance, to thereby determine a change in the attribute of the substance.

22. The method of claim 21 wherein the attribute is selected from the group consisting of a physical property, a chemical property, property, an electrical property, a magnetic property, an optical property, and a biological property.

23. The method of claim 21 wherein the substance is a single molecule or a group of molecules.

24. The method of claim 21 wherein the attribute is at least one of the following: a physical structure; a physical orientation; a chemical structure; a chemical composition; a chemical state; and an index of refraction.

25. The method of claim 21 wherein the substance is selected from the group consisting of a cell, an element, a compound, a molecule, a reactant, a solvent, a solute, a fluid, and a biological substance.

26. The method of claim 21 wherein the first plurality of photons has a wavelength in one of the following wavelength ranges: the infrared wavelength range; the near infrared wavelength range; the ultraviolet wavelength range; the X-ray wavelength range; and the visible wavelength range.

27. The method of claim 21 wherein the interaction of the first plurality of photons with the substance is selected from the group consisting of scattering, emission, reflection, and refraction.

28. The method of claim 21, further comprising:
detecting the filtered photons to provide therefrom a spectral image of the substance.

29. The method of claim 28 wherein the spectral image is one of the following: a Raman spectral image, a luminescence spectral image, a near infrared spectral image, an infrared spectral image, and an ultraviolet spectral image.

30. A system comprising:
a microfluidic circuit having a plurality of input channels integral thereto, wherein a first substance is provided through a first one of said plurality of input channels and a second substance is provided through a second one of said plurality of input channels;
a first photon source for providing a first plurality of photons through a third one of said plurality of input channels so as to internally illuminate a portion of said microfluidic circuit containing a mixture of said first and said second substances, wherein said first plurality of photons interact with said mixture while an attribute of at least one of said first and said second substances changes to thereby produce a second plurality of photons;
an optical lens for collecting said second plurality of photons;
a filter for receiving the collected photons and providing therefrom filtered photons having one or more predetermined wavelengths; and
a processor for determining an aspect of the filtered photons wherein the aspect of the filtered photons is a function of the attribute of at least one of said first and said second substances, to thereby determine a change in said attribute.

31. The system of claim 30, wherein said attribute is at least one of the following:
   a physical property, a chemical property, an electrical property, a magnetic property, an optical property, and a biological property.

32. The system of claim 30, further comprising:
   a second photon source placed external to said microfluidic circuit so as to externally illuminate said portion of said microfluidic circuit with a third plurality of photons, wherein a wavelength of said third plurality of photons is different from a wavelength of said first plurality of photons, and wherein said third plurality of photons interact with the mixture while said attribute of at least one of said first and said second substances changes to thereby produce a fourth plurality of photons,
   wherein said optical lens is configured to collect said fourth plurality of photons, and wherein said filter is configured to receive said collected fourth plurality of photons and provide therefrom said filtered photons to said processor.

* * * * *